(12) United States Patent
Sawa et al.

(10) Patent No.: US 7,942,831 B2
(45) Date of Patent: May 17, 2011

(54) MEASURING METHOD AND MEASURING DEVICE

(75) Inventors: Kenichi Sawa, Amagasaki (JP);
Yasunori Maekawa, Kobe (JP);
Yasuhito Ohnishi, Kakogawa (JP);
Katsutoshi Mishima, Sanda (JP)

(73) Assignee: Sysmex Corporation, Kobe (JP)

( * ) Notice: Subject to any disclaimer, the term of this patent is extended or adjusted under 35 U.S.C. 154(b) by 1057 days.

(21) Appl. No.: 11/789,373

(22) Filed: Apr. 24, 2007

(65) Prior Publication Data

US 2008/0021290 A1   Jan. 24, 2008

(30) Foreign Application Priority Data

Apr. 28, 2006   (JP) ................. 2006-124905

(51) Int. Cl.
*A61B 5/00*   (2006.01)
(52) U.S. Cl. ........................ 600/573; 600/345
(58) Field of Classification Search .................. 600/562, 600/573, 583, 584, 345
See application file for complete search history.

(56) References Cited

U.S. PATENT DOCUMENTS

| | | |
|---|---|---|
| 2003/0212379 A1 | 11/2003 | Bylund et al. |
| 2004/0249253 A1 | 12/2004 | Racchini et al. |
| 2005/0011759 A1 * | 1/2005 | Moerman et al. ........ 204/403.03 |

FOREIGN PATENT DOCUMENTS

| | | |
|---|---|---|
| CN | 1524496 A | 9/2004 |
| EP | 1552782 A1 | 7/2005 |
| EP | 1561418 A1 | 8/2005 |
| EP | 1623665 A1 | 2/2006 |
| WO | WO 98/24366 | 6/1998 |

OTHER PUBLICATIONS

Chinese Office Action for Corresponding Chinese Patent Application No. 200710098235.9 dated Oct. 17, 2008 and English translation thereof.
Partial European Search Report for Application No. EP 07008679 dated Sep. 10, 2007.

* cited by examiner

*Primary Examiner* — Max Hidenburg
*Assistant Examiner* — Jonathan M Foreman
(74) *Attorney, Agent, or Firm* — Brinks Hofer Gilson & Lione

(57) ABSTRACT

The present invention is to present a measuring device which can conduct stable extraction and measurement of interstitial fluid. The measuring device comprises: a device body which comprises an extraction part for extracting body fluid from a living body and a measuring part for measuring a biological component contained in the extracted body fluid; a holding member which holds the device body and has an opening part for defining a measurement area on the living body; and a mounting member for mounting the holding member on the living body; wherein the measurement area on the living body is defined by the opening part when the holding member is mounted on the living body by the mounting member.

17 Claims, 16 Drawing Sheets

MEASURING METHOD AND MEASURING DEVICE

RELATED APPLICATIONS

This application claims priority under 35 U.S.C. §119 to Japanese Patent Application No. JP2006-124905 filed Apr. 28, 2006, the entire content of which is hereby incorporated by reference.

FIELD OF THE INVENTION

The present invention relates to a method and a device for measuring a biological component contained in body fluid which is extracted from a living body.

BACKGROUND

U.S. Patent Publication No. 2004/0249253 discloses an example of a conventional biological component measuring device for measuring a biological component extracted from a living body.

The biological component measuring device disclosed in U.S. Patent Publication No. 2004/0249253 is provided with a disposable cartridge that includes a sampling module (extraction part) for extracting interstitial fluid (biological component) from the dermis layer of a patient and an analyzing module (measuring part) for analyzing glucose in the interstitial fluid, a local controller module which places the disposable cartridge inside and performs local controls, and a pair of straps (belts) for mounting the local controller module on the wrist. In this biological component measuring device, the local controller module is mounted on a wrist by wrapping the pair of straps (belts) around the wrist with a predetermined tension. Furthermore, in this biological component measuring device, a penetration member (needle) is inserted in the skin when the local controller module is mounted.

However, in the conventional biological component measuring device disclosed in U.S. Patent Publication No. 2004/0249253, since the local controller module is mounted on the wrist by wrapping a pair of straps (belts) around the wrist with a predetermined tension, the local controller module readily and disadvantageously moves in the circumferential direction of the wrist together with the pair of straps when the module is mounted. Furthermore, since a penetration member (needle) is inserted in the skin when the local controller module is mounted, the skin may be injured when the local controller module moves in this way. Therefore, a problem may arise in that it may be difficult to conduct stable extraction and measurement of interstitial fluid (biological component).

SUMMARY

A first aspect of the present invention is a measuring method for a biological component contained in body fluid which is extracted from a living body, comprising steps of: defining a measurement area on the living body by mounting a holding member to the living body by a mounting member, the holding member having an opening part for defining the measurement area on the living body and holding a device body which comprises an extraction part and a measuring part; forming a micropore in the measurement area defined by the opening part; contacting the extraction part of the device body with the micropore on the living body via the opening part; extracting body fluid from the micropore on the living body by the extraction part; and measuring the biological component contained in the body fluid by the measuring part.

A second aspect of the present invention is a measuring device, comprising: a device body which comprises an extraction part for extracting body fluid from a living body and a measuring part for measuring a biological component contained in the extracted body fluid; a holding member which holds the device body and has an opening part for defining a measurement area on the living body; and a mounting member for mounting the holding member on the living body; wherein the measurement area on the living body is defined by the opening part when the holding member is mounted on the living body by the mounting member.

A third aspect of the present invention is a measuring device, comprising: a device body which comprises an extraction part for extracting body fluid from a living body and a measuring part for measuring a biological component contained in the extracted body fluid; an area defining member which has an opening part for defining a measurement area on the living body and to which the device body is detachably attached; and a mounting member for mounting the area defining member on the living body; wherein the measurement area on the living body is defined by the opening part when the area defining member is mounted on the living body by the mounting member.

BRIEF DESCRIPTION OF THE DRAWINGS

FIG. 1 is a; FIG. 1 is a perspective view of an embodiment of the blood glucose level measuring device of the present invention;

DETAILED DESCRIPTION OF THE PREFERRED EMBODIMENTS

An embodiment of the present invention is described hereinafter based on the drawings.

The general structure of a blood glucose level measuring device 100 of the embodiment is first described with reference to FIGS. 1 through 10.

Figure 1:
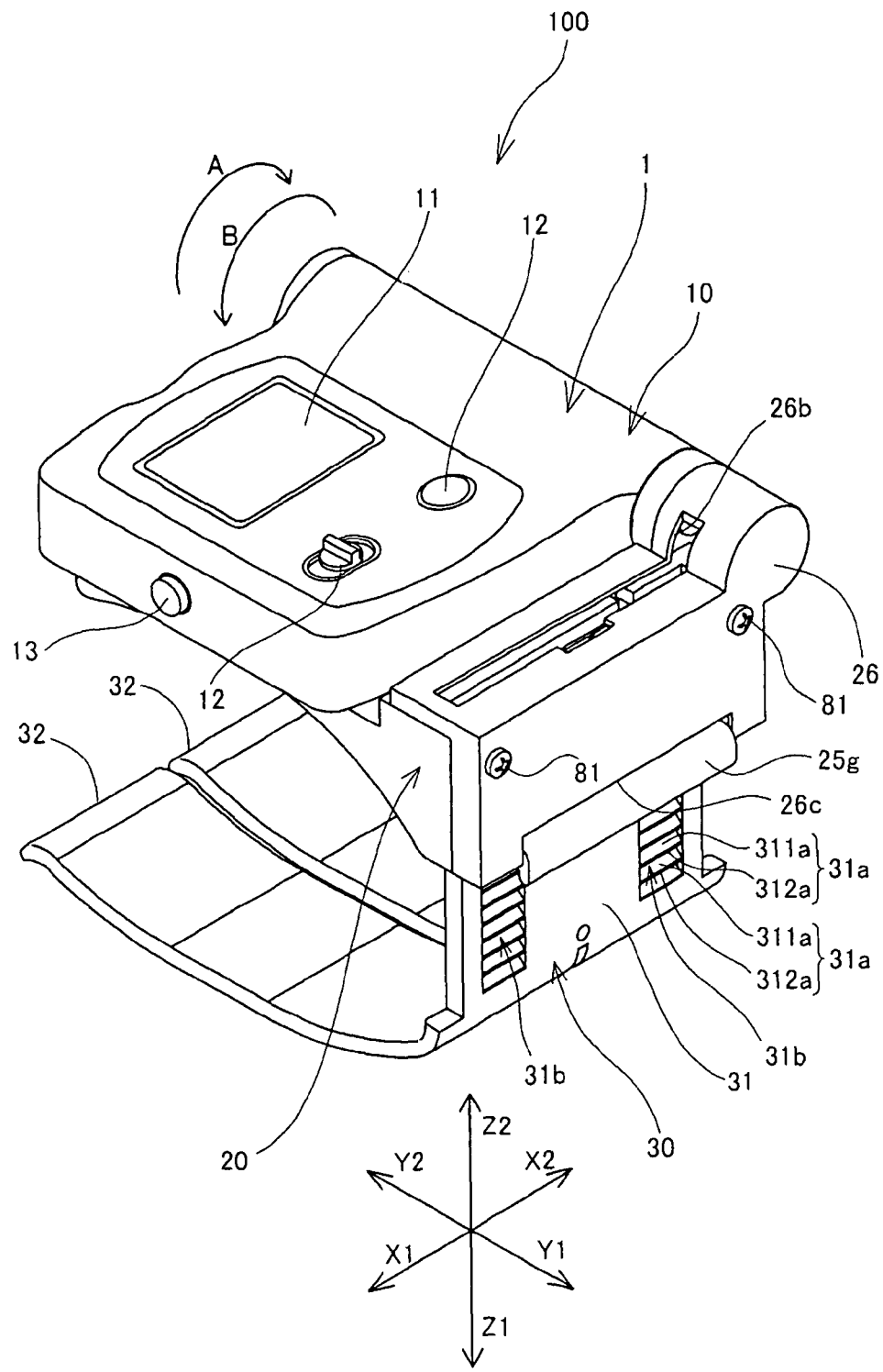
Figure 2:
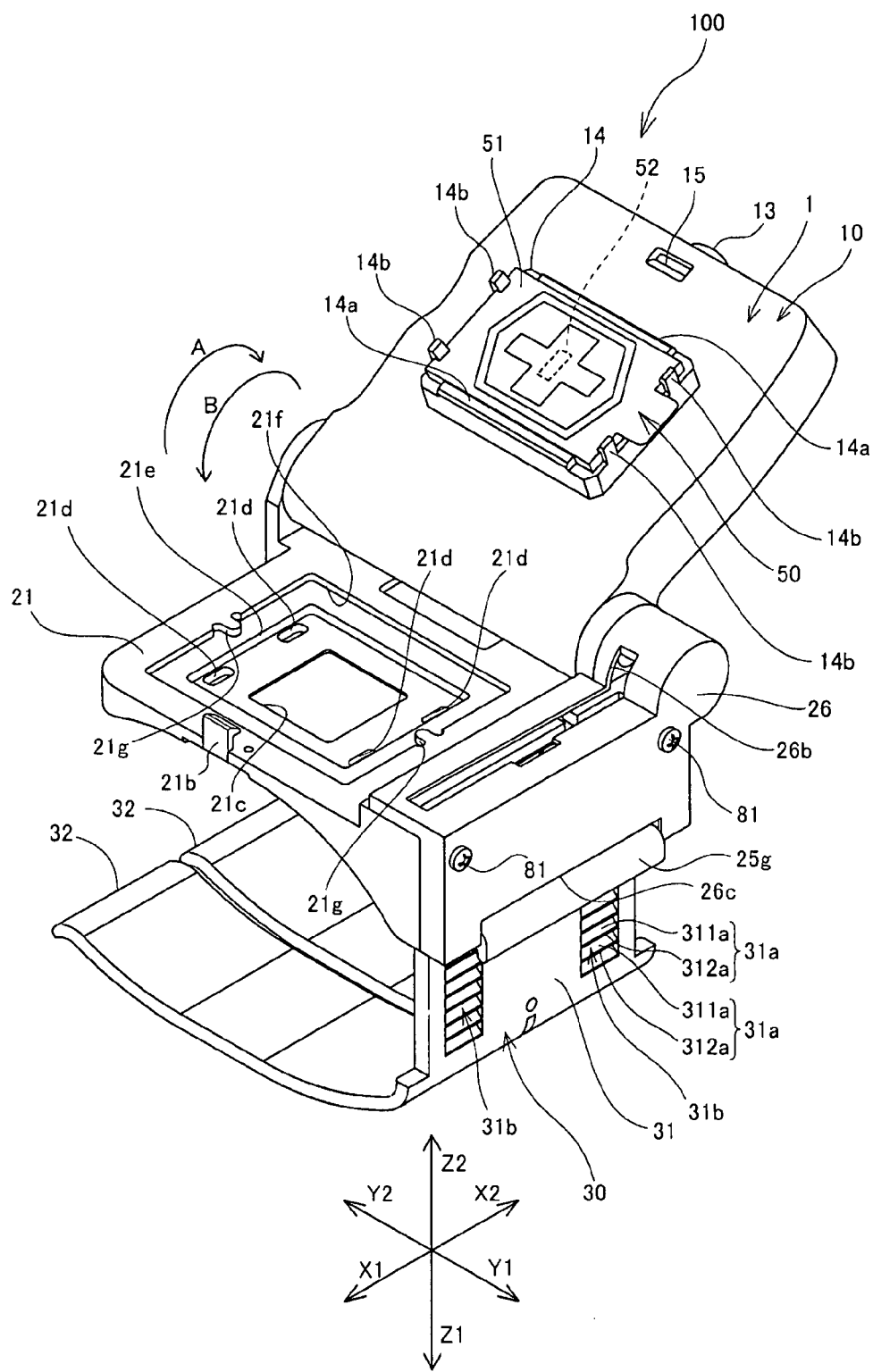
FIG. 2 is a perspective view of the embodiment of the blood glucose level measuring device of FIG. 1 with the device body in an open condition.

The blood glucose level measuring device 100 of the present embodiment extracts glucose as a biological component from a living body and calculates the blood glucose level by analyzing the extracted glucose. The blood glucose level measuring device 100 is provided with an analyzing unit 1, and extraction cartridge 50 (refer to FIG. 2) as shown in FIGS. 1 and 2. The analyzing unit 1 includes a device body 10 for detachably holding the extraction cartridge 50, holding member 20 for holding the device body 10 so as to be rotatable, and a mounting member 30 for mounting the holding member 20 on the wrist 110 of a subject.

Figure 3:
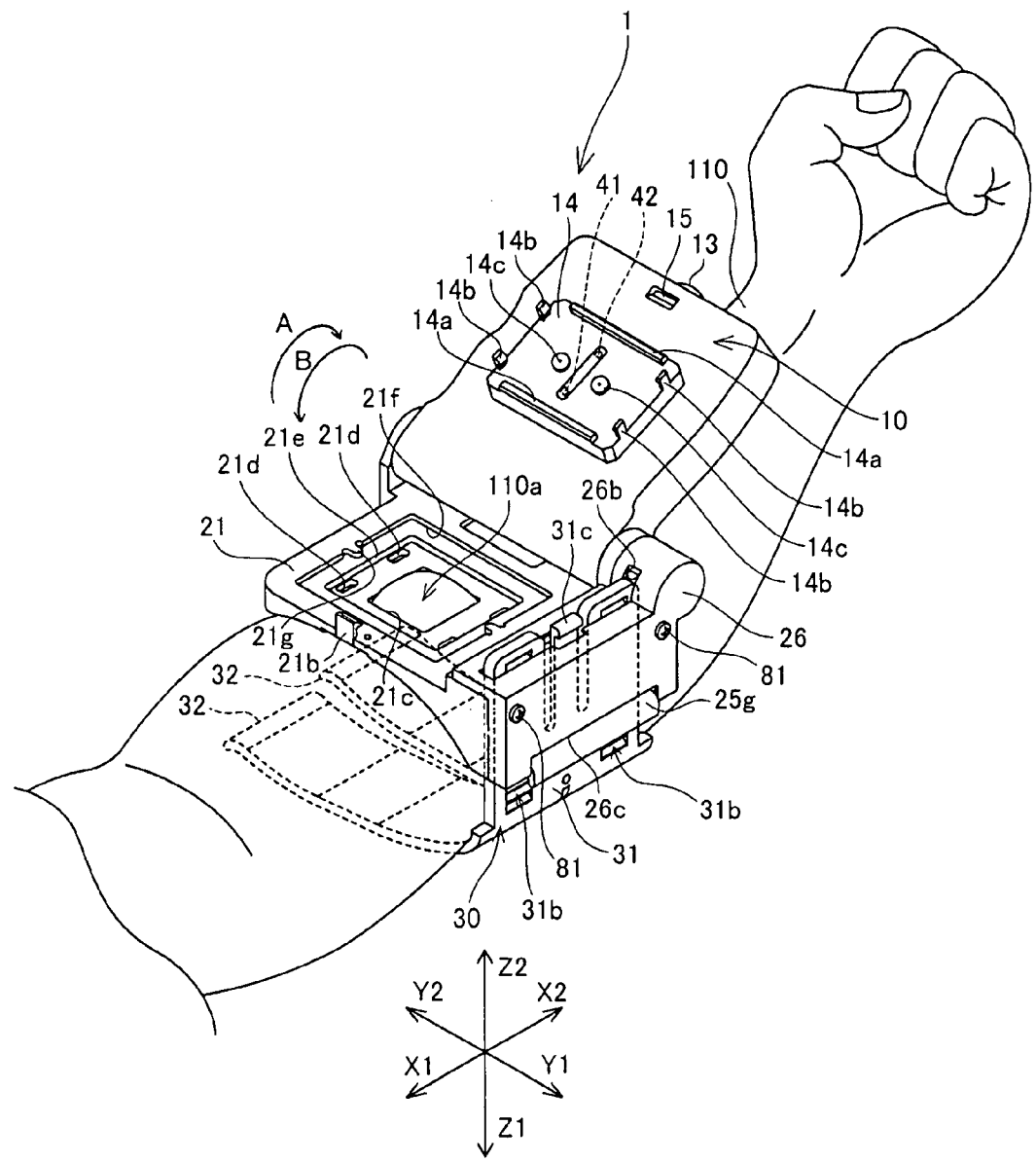
FIG. 3 is a perspective view of the embodiment of the blood glucose level measuring device of FIG. 1 with the analyzing unit mounted on the wrist of a subject.
Figure 4:
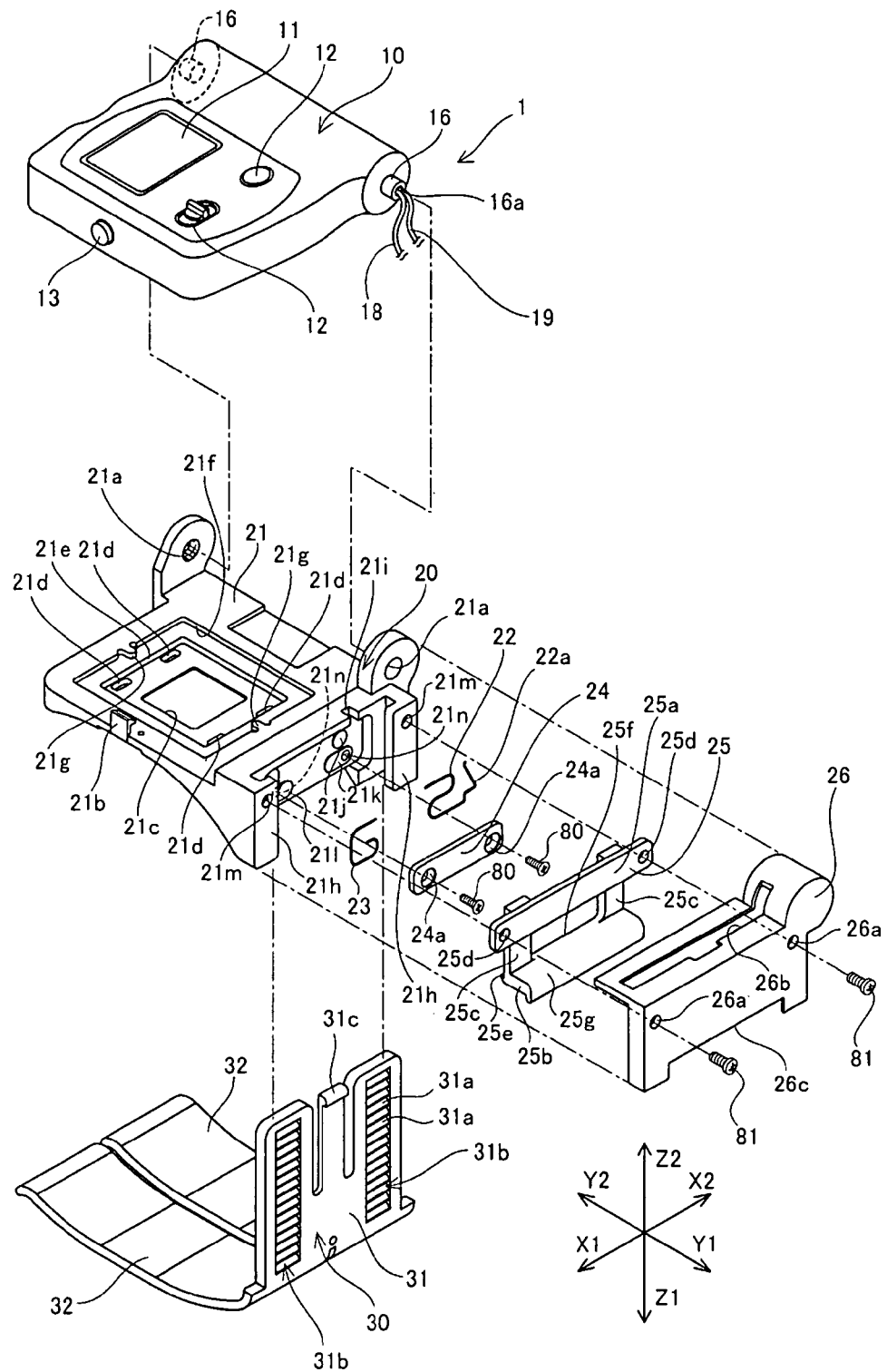
FIG. 4 is an exploded perspective view of the embodiment of the blood glucose level measuring device of FIG. 1.

As shown in FIGS. 3 and 4, the device body 10 of the analyzing unit 1 includes a display 11 and operation button 12 disposed on the front surface, release button 13 disposed on the end side in the arrow X1 direction, extraction cartridge attachment part 14 and connector hole 15 provided on the reverse side, a pair of rotating shafts 16 disposed on the end side in the arrow X2 direction, and a direct current type constant-voltage regulated power supply 17 (refer to FIG. 10) provided internally. The display 11 of the device body 10 is provided to display the amount of glucose and blood glucose level calculated by a controller (not shown in the drawings). The operation button 12 of the device body 10 is provided to control the operation of the blood glucose level measuring device 100, such as starting measurement and the like. The release button 13 of the device body 10 is provided to release the engagement of a connector 21a of the holding member 20 described later and the connector hole 15 of the device body 10.

Figure 10:
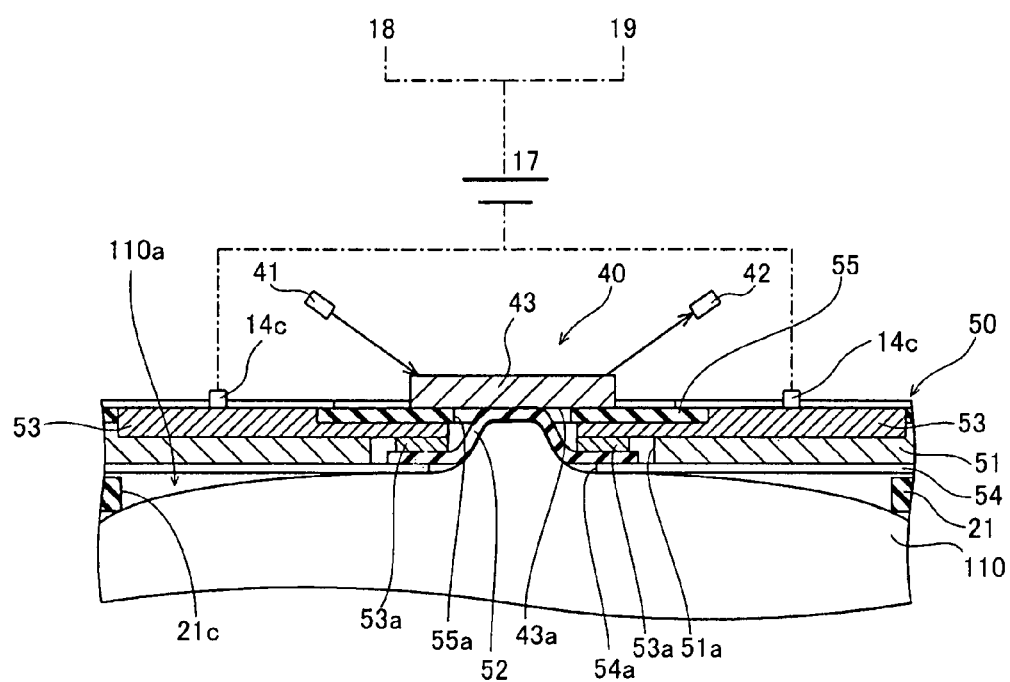
FIG. 10 is an expanded view showing the embodiment of the blood glucose level measuring device of FIG. 1 mounted on the wrist of a subject.

As shown in FIG. 3, the extraction cartridge attachment part 14 includes a pair of rib-like projecting parts 14a which function as guides when attaching the extraction cartridge 50, four connector 14b for attaching the extraction cartridge 50, a pair of terminals 14c connected to the negative pole of the constant voltage regulated power supply 17 (refer to FIG. 10) of the device body 10, and a light source 41 and photoreceptor 42 which configure a detecting part 40 (refer to FIG. 10). The four connectors 14b of the extraction cartridge attachment part 14 are formed elastically deformable such that the extraction cartridge 50 can be detachably attached on.

The connector hole 15 of the device body 10 (refer to FIG. 10) is provided to engage the connector 21b of the holding member 20 which is described later when the device body 10 is in a closed condition on the holding member 20. The pair of rotating shafts 16 of the device body 10 are provided so as to protrude to the exterior sides, as shown in FIG. 4. A hole 16a is provided in the rotating shaft 16 on the arrow Y1 side that extends along the rotating shaft 16. The hole 16a of the rotating shaft 16 is provided to allow cables 18 and 19 to extend to the exterior from the interior part of the device body 10. The cables 18 and 19 of the device body 10 are respectively connected to the positive pole of the constant voltage regulated power supply 19 (refer to FIG. 10).

In the present embodiment the holding member 20 includes a holding member body 21 for holding the device body 10 so as to be rotatable, contact terminals 22 and 23 which are respectively connected to the cables 18 and 19 of the device body 10, fix member 24 for fixing the contact terminals 22 and 23 on the holding member body 21, engage member 25 which configures a ratchet mechanism, and cover member 26 for covering one end of the holding member body 21 (the end in the arrow Y1 direction), as shown in FIG. 4.

In the present embodiment the holding member body 21 of the holding member 20 includes a pair of rotating shaft insertion holes 21a on the end in the arrow X2 direction, connector 21b provided on the end in the arrow X1 direction, open part 21c provided near the center when viewed planimetrically, and four spaces 21d and stepped parts 21e and 21f. The holding member body 21 is formed of ABS resin or the like. The bottom surface of the holding member body 21 is configured in an arc shape when viewed from the X2 direction so as to improve contact with the wrist 110 of a subject when the holding member 20 is mounted on the wrist 110 of the subject.

The pair of rotating shafts 16 of the device body 10 are respectively inserted in the pair of rotating shaft holes 21a of the holding member body 21 so that the device body 10 is rotatable in the A direction and B direction (refer to FIGS. 1 and 2) relative to the holding member body 21. The connector 21b of the device holding member body 21 (refer to FIG. 2) functions to limit rotation of the device body 10 in the A direction (opening direction) relative to the holding member body 21 by engaging the connector hole 15 (refer to FIG. 2) of the device body 10 when the device body 10 is in a closed condition on the holding member 20. At this time, if the extraction cartridge 50 is attached on the device body 10, the extraction cartridge 50 makes contact with the surface of the wrist 110 of the subject which is exposed through the open part 21c of the holding member body 21, as shown in FIG. 10.

In the present embodiment the open part 21c of the holding member body 21 has a square shape viewed planimetrically, as shown in FIG. 3. The open part 21c functions to define the measuring area 110a of the subject's wrist 110 when the holding member 20 is mounted on the wrist 110 of the subject via the mounting member 30. At this time the measuring area 110a on the wrist 110 of the subject expands in the arrow Z2 direction through the open part 21c.

The four spaces 21d (refer to FIG. 3) of the holding member body 21 are provided to accommodate four connectors 14b (refer to FIG. 4) of the device body 10 when the device body 10 is in a closed condition on the holding member 20 (refer to FIG. 1). The stepped part 21d (refer to FIG. 3) of the holding member body 21 is provided to accommodate the extraction cartridge 50 (refer to FIG. 3) of the device body 10 when the device body 10 is in a closed condition on the holding member 20 (refer to FIG. 1). A pair of projections 21g are provided on the stepped part 21f of the holding member body 21. The stepped part 21f and projections 21g function to position the micropore forming device 120, which is described later, relative to the holding member 20.

Figure 5:
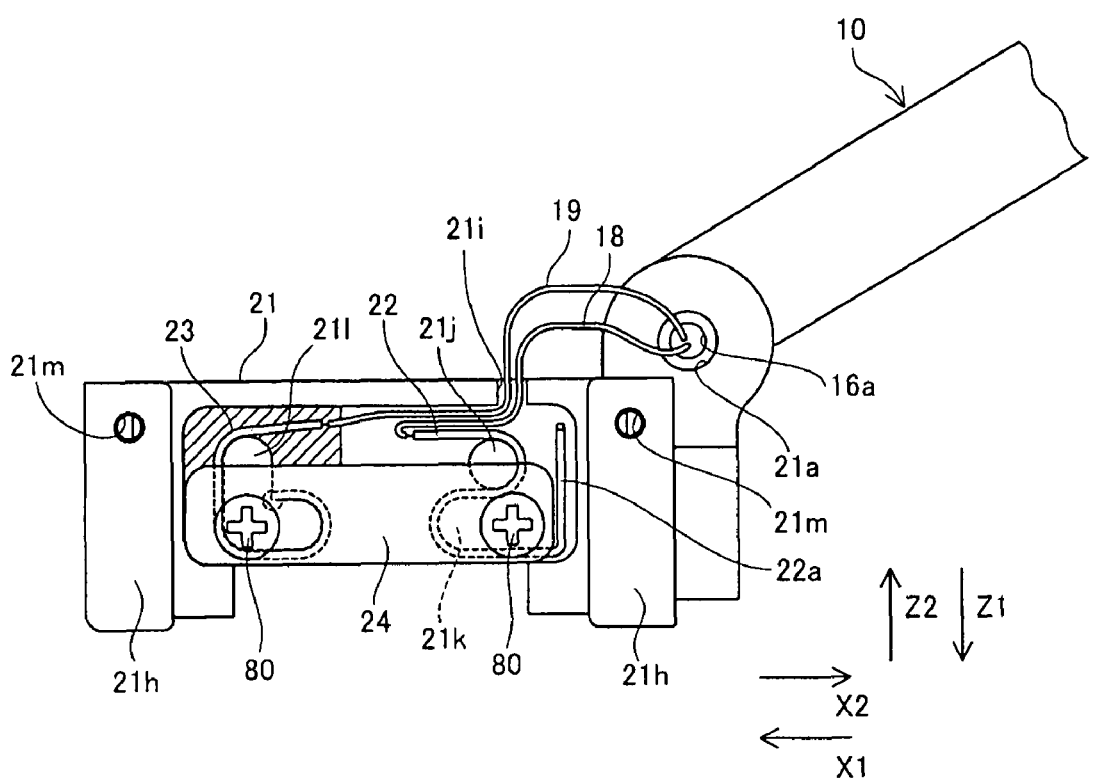
FIG. 5 is a side view showing the embodiment of the blood glucose level measuring device of FIG. 1 with the mounting member, cover member, and connecting member detached from the analyzing unit.
Figure 6:
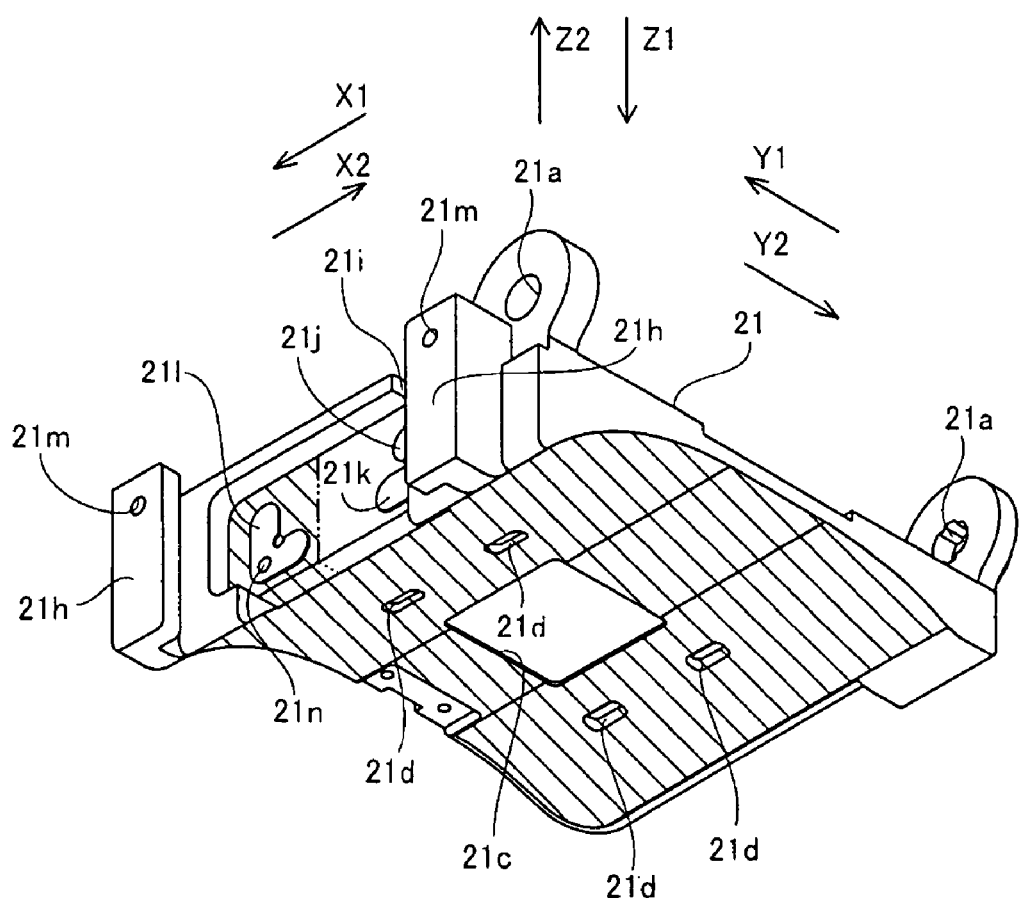
FIG. 6 is a perspective view of the embodiment of the blood glucose level measuring device of FIG. 1 showing the holding member body.

In the present embodiment one end of the holding member body 21 (the end in the arrow Y1 direction) is provided with a pair of guides 21h, notches 21l for the disposition of the cables 18 and 19 of the device body 10, circular projection 21j, ovoid projection 21k, and L-shaped projection 21l, as shown in FIGS. 4 through 6.

In the present embodiment the pair of guides 21h of the holding member body 21 functions to slidably guide the mounting member 30 in the arrow Z1 and arrow Z2 directions. Moreover, screw holes 21m are formed in the respective pair of guides 21h. Screw holes 21n are respectively provided on the ovoid projection 21k and L-shaped projection 21l of the holding member body 21. Gold plating is provided on the periphery of the L-shaped projection 21*l* and the bottom surface of the holding member body 21 (cross hatched (diagonally shaded) regions of FIGS. 5 and 6). Thus, the holding member body 21 is configured so as to be usable as an electrode.

In the present embodiment the contact terminals 22 and 23 are formed of conductive material such as metal or the like. As shown in FIG. 5, the contact terminal 22 is disposed along periphery of the circular projection 21*j* and ovoid projection 21*k* of the holding member body 21. The contact terminal 22 is provided with a contact part 22*a* formed so as to project in the arrow Y1 direction of FIG. 4. Further, the contact terminal 23 is disposed along periphery of the L-shaped projection 21*l* of the holding member body 21. Thus, since the conductive contact terminal 23 makes contact with the gold plating of the holding member body 21, the gold-plated region of the holding member body 21 is connected to the positive pole of the constant voltage regulated power supply 17 (refer to FIG. 10).

In the present embodiment the fix member 24 of the holding member 20 is formed of ABS resin or the like. The fix member 24 has two screw holes 24*a*, as shown in FIG. 4. The fix member 24 is attached to the holding member body 21 by screws 80 which are tightened in the screw hole 21*n* through the screw insertion hole 24*a*. Thus, the contact terminals 22 and 23, which are disposed between the fix member 24 and the holding member body 21, are fixed on the holding member body 21.

Figure 7:
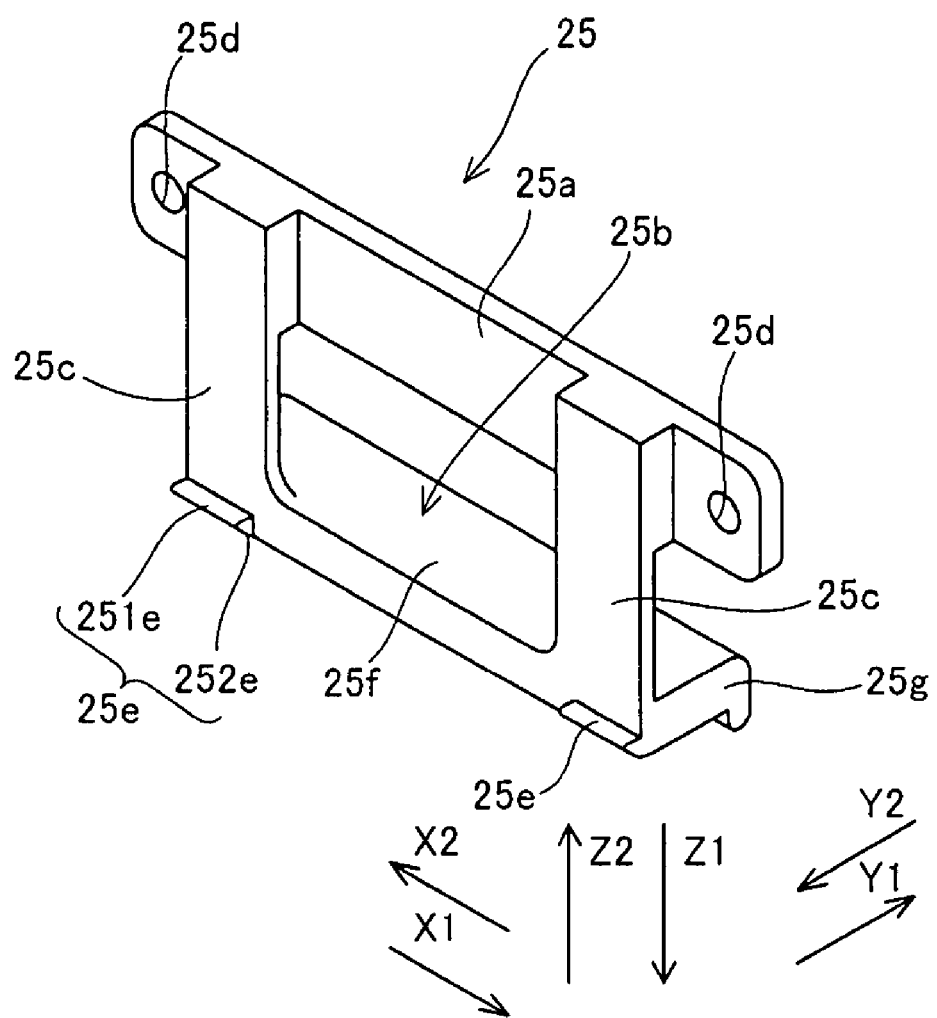
FIG. 7 is a perspective view of the embodiment of the blood glucose level measuring device of FIG. 1 showing the connecting member.

In the present embodiment, as shown in FIGS. 4 and 7, the engage member 25 of the holding member 20 includes a attaching part 25*a* and moving part 25*b* extending in the X2 direction, and a pair of connecting parts 25*c* connecting the attaching part 25*a* and moving part 25*b* and extending in the Z2 direction. The engage member 25 is formed of polyacetal resin. Thus, the mounting member 30 in contact with the engage member 25 is slidable, and the pair of connector parts 25*c* are elastically deformable. The engage member 25 configures a ratchet mechanism that unidirectionally regulates the moving direction of the mounting member 30 relative to the holding member 20 (arrow Z2 direction). The engage member 25 has a release function to release the regulation of the ratchet mechanism.

In the present embodiment the attaching part 25*a* of the engage member 25 has a pair of screw insertion holes 25*d* at both ends. The moving part 25*b* of the engage member 25 includes a pair of hooks 25*e* that projects in the Y2 direction, locking part 25*f* to prevent the mounting member 30 from falling, and a grip part 25*g* for gripping when the moving part 25*b* is moved in the arrow Y1 direction. The pair of hooks 25*e* of the moving part 25*b* includes a top part 251*e* that is a horizontal surface extending in the arrow Y2 direction (horizontal direction) and a bottom part 252*e* that is an inclined surface which inclines at a predetermined angle relative to the arrow Z2 direction when viewed from the arrow X2 direction.

In the present embodiment the locking part 25*f* of the moving part 25*b* is provided to engage a locking connector 31*c* of the mounting member 30 which is described later when the regulation by the ratchet mechanism is released. The grip part 25*g* of the moving part 25*b* is provided to release the regulation of the ratchet mechanism. Specifically, the regulation of the ratchet mechanism can be released by moving the grip part 25*g* in the arrow Y1 direction to release the engagement of the hook 31*a* of the mounting member 30 which is described later and the hook 25*e* of the engage member 25.

Figure 8:
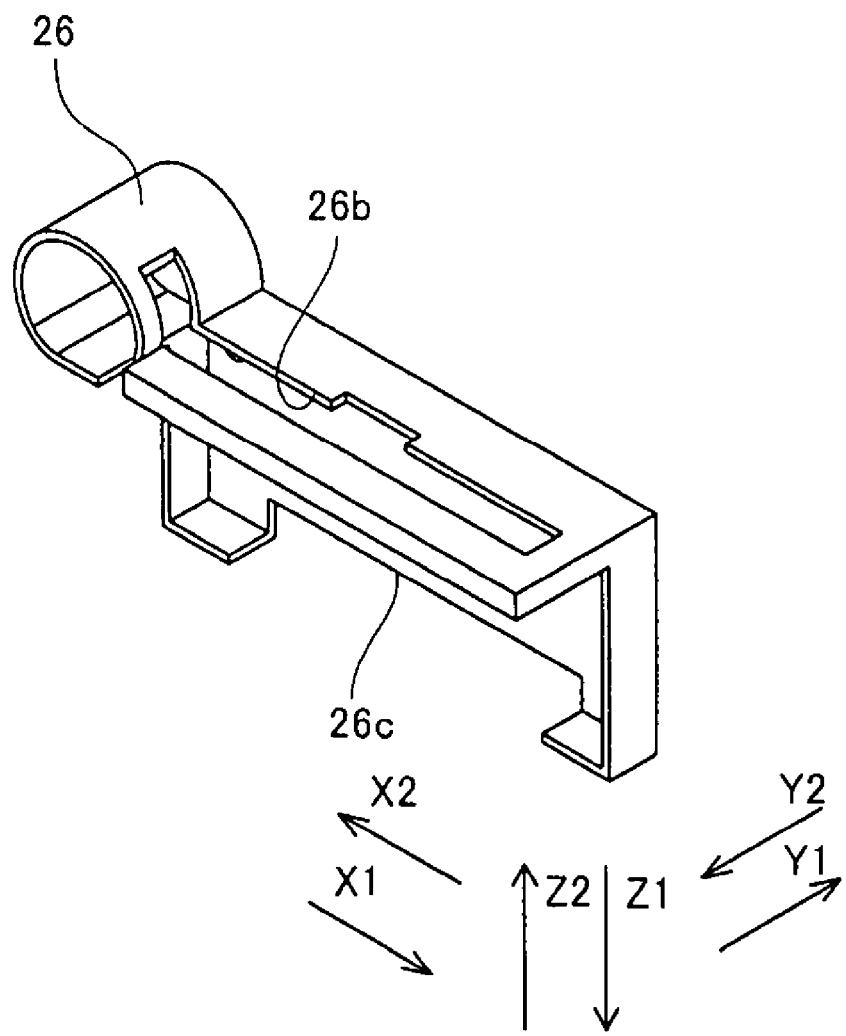
FIG. 8 is a perspective view of the embodiment of the blood glucose level measuring device of FIG. 1 showing the cover member.

As shown in FIGS. 4 and 8, in the present embodiment the cover member 26 of the holding member 20 includes a pair of screw insertion holes 26*a*, through hole 26*b* which the mounting member 30 passes through, and a notch 26*c* for the disposition of the engage member 25. The cover member 26 is formed of ABS resin or the like. The cover member 26 and engage member 25 are attached to the holding member body 21 when a screw 81 is tightened in the screw hole 21*m* of the holding member body 21 through the screw insertion holes 26*a* and 25*d*. The cover member 26 functions to regulate the amount of movement of the moving part 25*b* of the engage member 25 in the arrow Y1 direction. Thus, the lock connector 31*c* of the mounting part described later invariably engages the locking part 25*f* of the engage member 25 since the locking part 25*f* of the moving part 25*b* is prevented from moving in the arrow Y1 direction when the moving part 25*b* is moved in the arrow Y1 direction and the regulation of ratchet mechanism is released.

Figure 9:
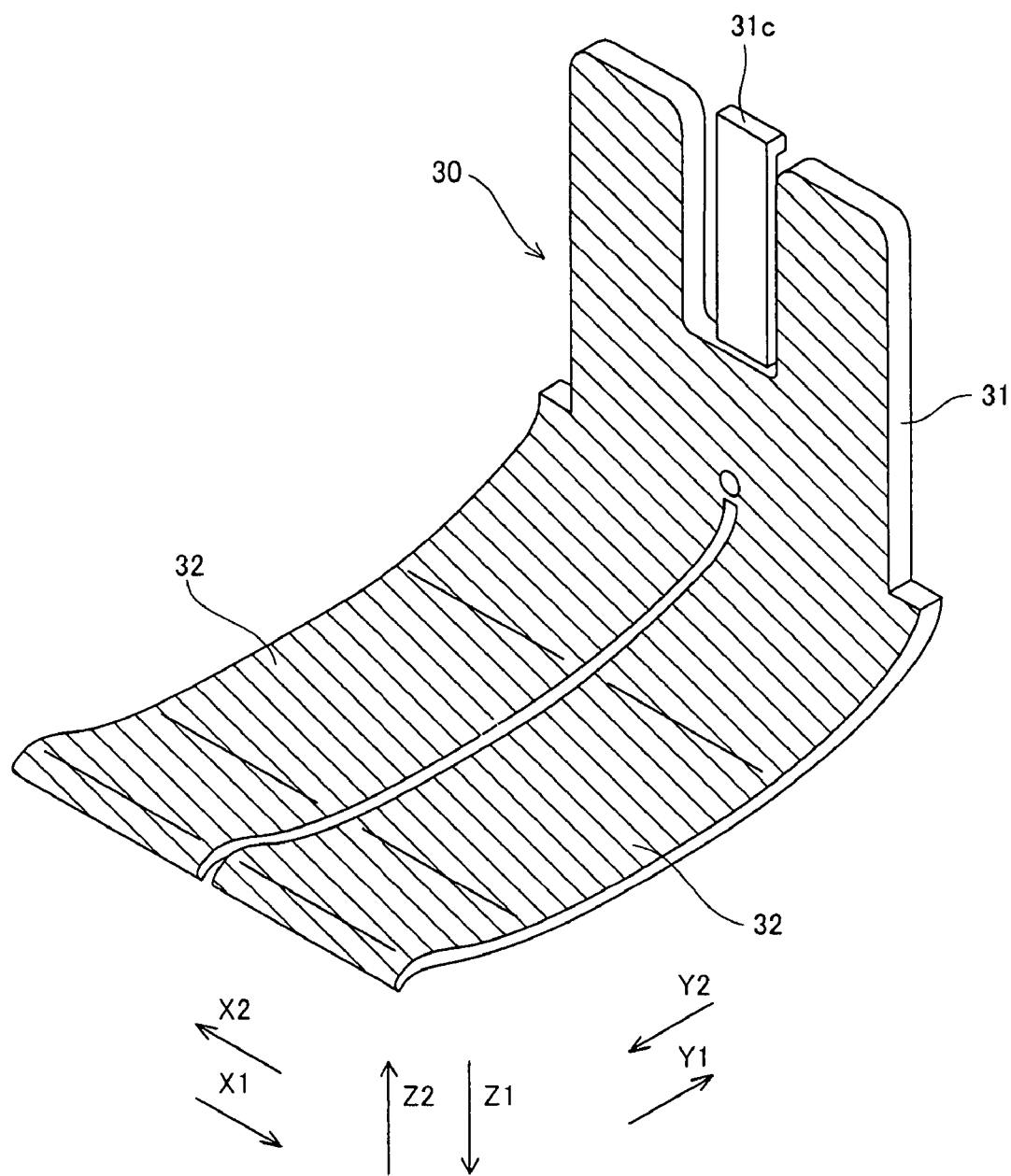
FIG. 9 is a perspective view of the embodiment of the blood glucose level measuring device of FIG. 1 showing the mounting member.

As shown in FIGS. 4 and 9, in the present embodiment the mounting member 30 includes a connector part 31 for guiding the holding member body 21 to the guide 21*h*, and two tightening parts 32 extending in the arrow Y2 direction from the bottom end of the connector part 31. Thus, the mounting member 30 and one end of the holding member 20 (the end on the arrow Y1 direction) are linked, and the mounting member 30 and the other end of the holding member 20 (the end in the arrow Y2 direction) are mutually separated. The mounting member 30 is formed of ABS resin or the like. Gold plating is applied to the inner surface (cross hatched area (diagonal line shaded area) shown in FIG. 9) of the mounting member 30. Thus, the mounting member 30 is configured so as to be usable as an electrode. The gold plated area of the mounting member 30 is connected to the positive pole of the constant voltage regulated power supply 17 (refer to FIG. 10) since the contact part 22*a* extending in the arrow Y1 direction from the contact terminal 22 formed of conductive material such as metal or the like makes contact with the gold plated area of the mounting member 30. The mounting member 30 configures the previously mentioned ratchet mechanism.

In the present embodiment the connector part 31 of the mounting member 30 includes a pair of connecting areas 31*b* having a plurality of hooks 31*a*, and the locking part 31*c*. The connector part 31 is configured so as to change the distance between the tightening parts 32 and the holding member 20. The plurality of hooks 31*a* of the connecting part 31 are adjacent in the arrow Z2 direction. The hook 31*a* protrudes in the arrow Y1 direction, and, viewed from the arrow X2 direction, includes a top surface 311*a* (refer to FIG. 1) which is inclined at a predetermined angle relative to the arrow Z1 direction, and a bottom surface 312*a* (refer to FIG. 1) that is horizontal and extends in the arrow Y1 direction (horizontal direction). Thus, when the mounting member 30 is pressed in the arrow Z2 direction relative to the holding member 20, the inclined top surface 311*a* (refer to FIG. 1) of the hook 31*a* of the mounting member 30 contacts the inclined bottom surface 252*e* (refer to FIG. 7) of the hook 25*e* of the holding member 20, and the moving part 25*b* of the engage member 25 moves in the arrow Y1 direction causing the mounting member 30 to slide in the arrow Z2 direction (upward direction) relative to the holding member 20. On the other hand, when the mounting member 30 is pressed in the arrow Z1 direction relative to the holding member 20, the horizontal bottom surface 312*a* (refer to FIG. 1) of the hook 31*a* of the mounting member 30 contacts the horizontal top surface 251*e* (refer to FIG. 7) of the hook 25*e* of the holding member 20, and it is possible to regulate the moving of the mounting member 30 in the arrow Z1 direction (downward direction) relative to the holding member 20.

In the present embodiment the tightening parts 32 of the mounting member 30 is arc-shaped when viewed from the arrow X2 direction, and is configured so as to be elastically deformable. The tightening parts 32 tighten the wrist 110 of the subject from above and below between the tightening parts 32 and holding member 20 by changing the distance between the tightening parts 32 and holding member 20 via the connector part 31.

The extraction cartridge 50 includes, as shown in FIG. 10, a cartridge body 51 formed of acrylic resin or the like, mesh sheet 52 which functions as a medium for retaining a fluid, a pair of electrodes 53, sensor member 43 configuring a detecting part 40 for detecting glucose, two-sided tape 54, and electrode sheet 55 which is essentially an insulating body. A through hole 51a is formed in the cartridge body 51. The mesh sheet 52 and a pair of active carbon electrodes 53a are retained within the through hole 51a. The electrode sheet 55 is disposed between the electrode 53 and sensor member 43. A measuring surface 43a of the sensor member 43 is exposed to the mesh sheet 52 side via an open part 55a of the electrode sheet 55.

The mesh sheet 52 makes contact with the bottom surface of the active carbon electrode 53a, and is attached to the bottom surface of the cartridge body 51 by the two-sided tape 54. The two-sided tape 54 has an open part 54a for the disposition of the mesh sheet 52, and is adhered along the entire bottom surface of the cartridge body 51. The mesh sheet 52 contains fluid during glucose extraction. The mesh sheet 52 is configured so as to make contact with the bottom surface of the sensor member 43 when the upward expansion of the skin on the wrist 110 of a subject causes the skin to push through the open part 54a of the two-sided tape 54.

The electrode 53 is connected to the negative pole of the constant voltage regulated power supply 17 when the extraction cartridge 50 is attached on the device body 10 and makes contact with the terminal 14c. Described below is the mechanism for collecting body fluid to the fluid retained in the mesh sheet 52 by applying a voltage between the electrode 53 of the extraction cartridge 50 and the holding member body 21 and mounting member 30. When a voltage is supplied by the constant voltage regulated power supply 17, the electrode 53 on the negative pole side has a negative (−) charge. The active carbon electrodes 53a adhered below the electrode 53 have polarity. Therefore, the internal bottom part of the active carbon electrode 53a of the electrode 53 has a negative (−) charge. Thus, the sodium ions (Na+) contained in the extracted body fluid migrate toward the active carbon electrode 53a and into the fluid retained in the mesh sheet 52. Biological component such as glucose and the like within the body fluid migrates to the fluid retained in the mesh sheet 52 in conjunction with the migration of the sodium ions (Na+) within the body fluid. The biological component such as glucose and the like reaches the measuring surface 43a of the sensor member 43.

As shown in FIG. 10, the sensor member 43 is disposed on the top surface of the electrode sheet 55. The bottom side of the sensor member 43 has a measuring surface 43a. The measuring surface 43a is subjected to processing in which a gel containing a color-producing agent which reacts with glucose and a predetermined enzyme are applied, and thereafter the gel is dried.

Specifically, the measuring surface 43a of the sensor member 43 is treated by a process in which a gel is applied then dried, the gel containing a mixture of the oxidizing enzyme glucose oxidase (GOD) as a glucose catalyst, an oxidoreductase peroxidase (POD) as a catalyst for hydrogen peroxide ($H_2O_2$) which is generated via the reaction of the glucose with the GOD catalyst, and a color-producing agent that generates a color in reaction to the O* (active oxygen) produced by the reaction of $H_2O_2$ and POD catalyst.

The use sequence of the blood glucose level measuring device 100 of the embodiment is described below with reference to FIGS. 10 through 15.

Figure 11:
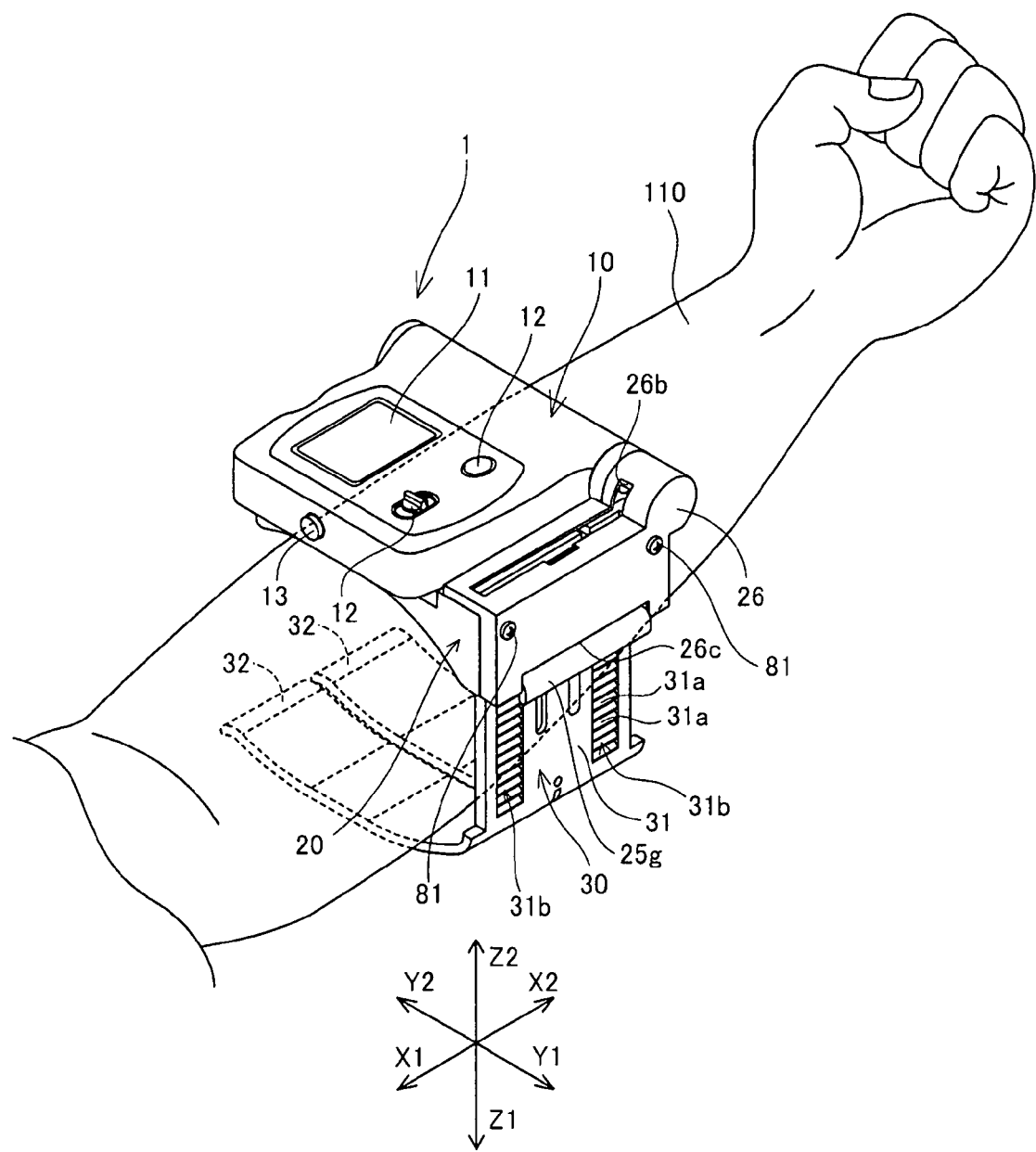
FIGS. 11 through 13 and FIG. 15 illustrate the sequence of use of the embodiment of the blood glucose level measuring device of FIG. 1.

In the present embodiment the analyzing unit 1 is moved in the arrow Y2 direction from the side that the holding member 20 and tightening parts 32 are separated so as to position the wrist 110 of the subject between the holding member 20 and the tightening parts 32 of the mounting member 30, as shown in FIG. 11. Then, the gold plated bottom surface of the holding member body 21 of the holding member 20 is disposed so as to make contact with the wrist 110 of the subject.

Figure 12:
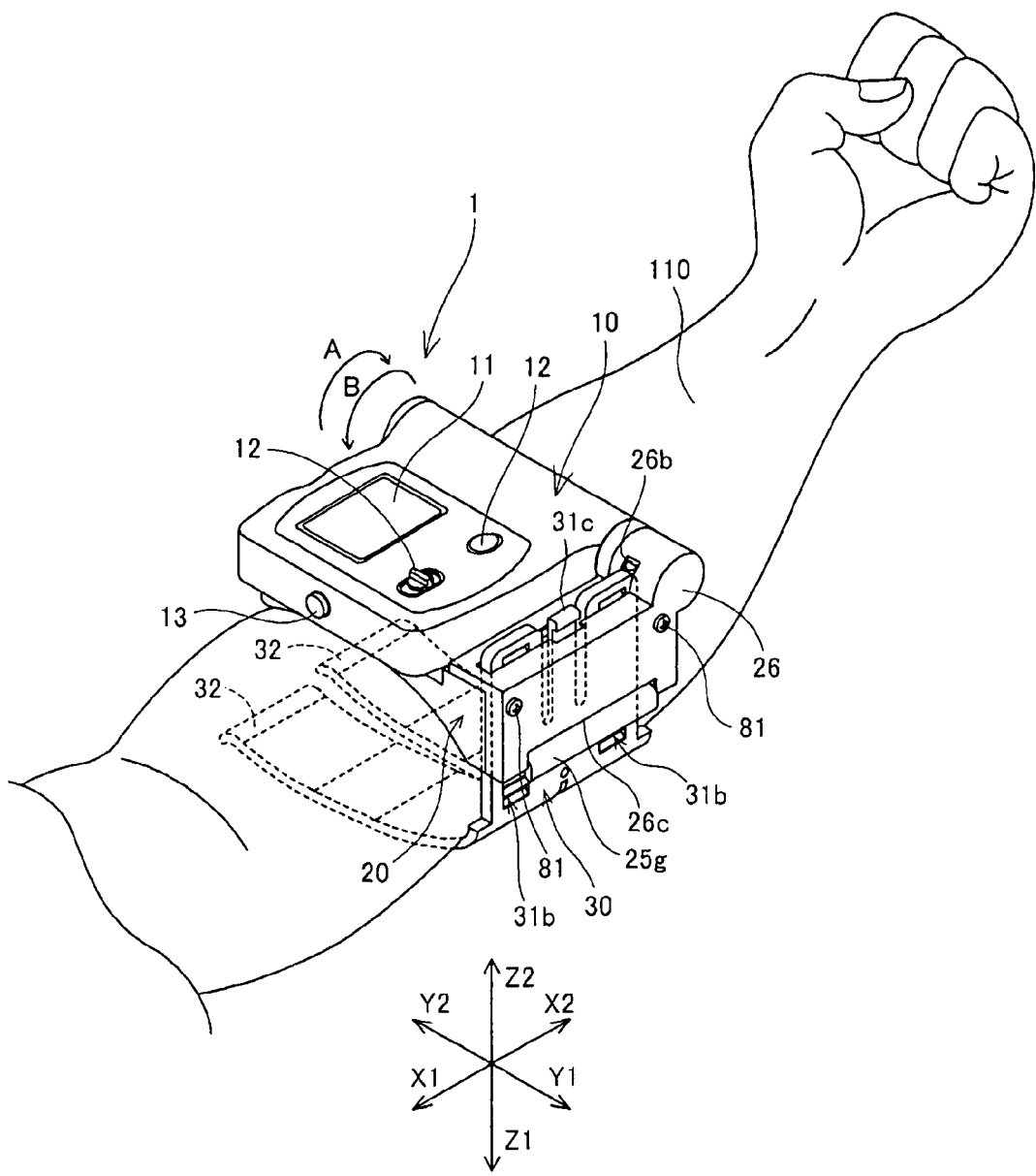

In the present embodiment the mounting member 30 is moved in the arrow Z2 direction relative to the holding member 20, as shown in FIG. 12. Thus, the analyzing unit 1 is mounted on the wrist 110 of the subject. The top end of the connector part 31 of the mounting member 30 is disposed at the through hole 26b of the cover member 26 at this time. The two tightening parts 32 configured of ABS resin or the like are respectively elastically deformed and the gold plated inner surfaces make contact with the wrist 110 of the subject. The measurement area 110a is defined by the open part 21c of the holding member 20 when mounted in the manner described above. Thereafter, with the connector part 21b of the holding member body 21 and connector hole 15 engaged (refer to FIG. 13), device body 10 is rotated in the A direction by pressing the release button 13 of the device body 10.

Figure 13:
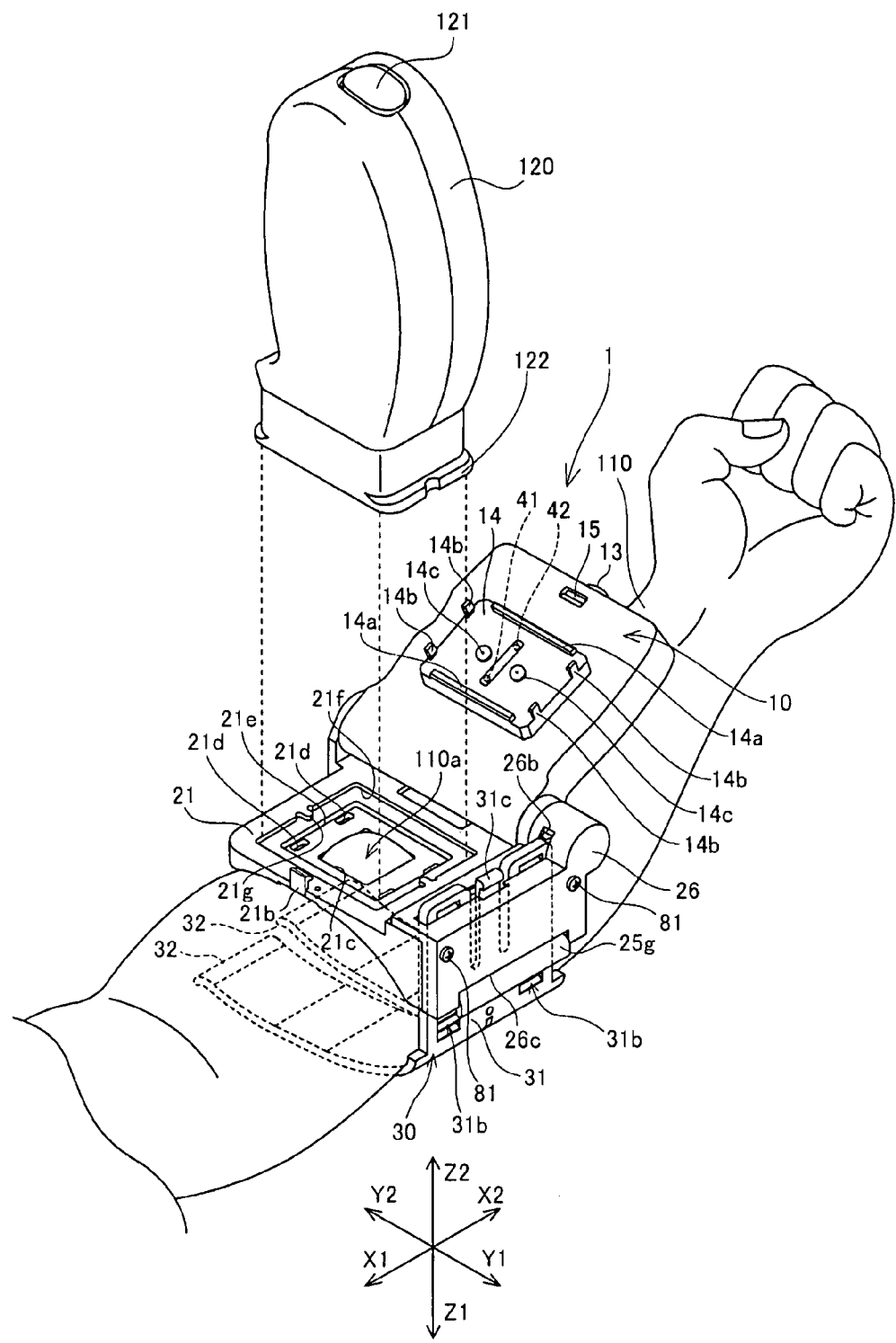
Figure 14:
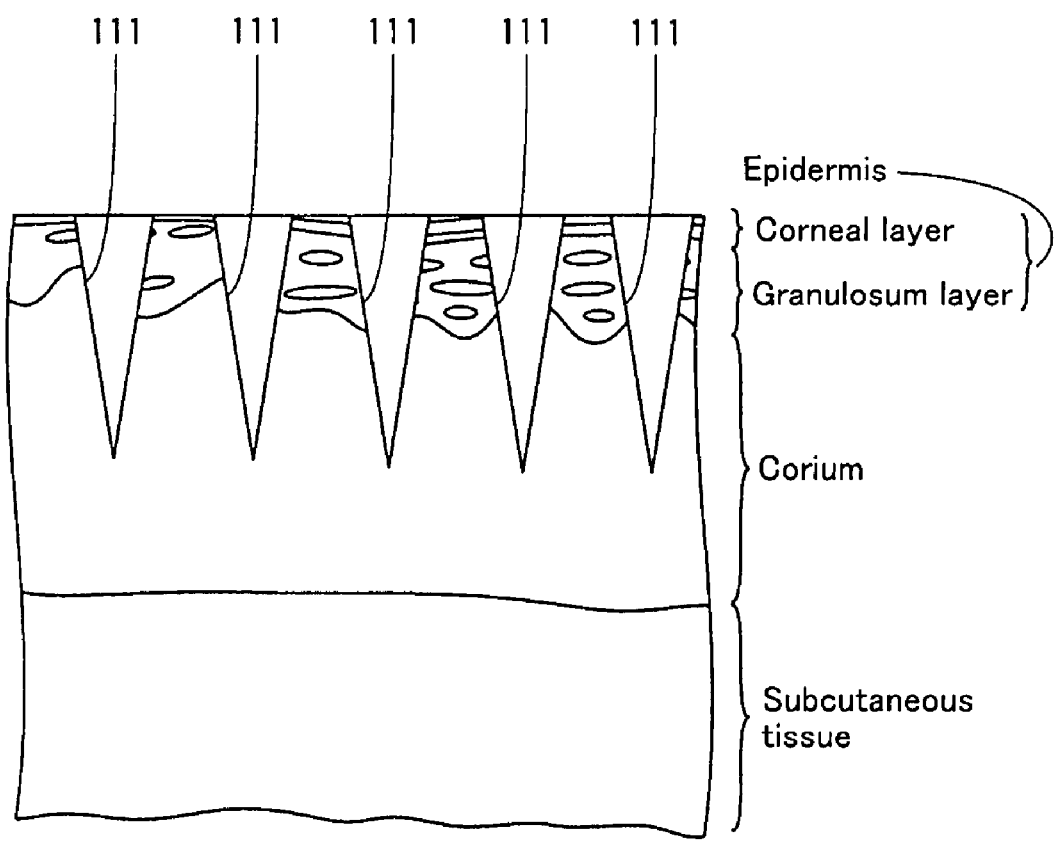
FIG. 14 is a cross section view showing the condition of the skin in which micropores are formed by the micropore forming device of FIG. 13.

In the present embodiment the micropore forming device 120 forms micropores (extraction holes) 111 (refer to FIG. 14) in the measurement area 110a defined by the open part 21c of the wrist 110 of the subject, as shown in FIG. 13. The micropore forming device 120 is provided with a button 121 and guide 122. Then, the guide 122 of the micropore forming device 120 is disposed at the projection 21g and stepped part 21f of the holding member body 21. Thus, the micropore forming device 120 is positioned with respect to the holding member body 21. Thereafter, when the button 121 is pressed, micropores (extraction holes) 111 (refer to FIG. 14) are formed in the measurement area 110a defined by the open part 21c on the wrist 110 of the subject by extending the microneedles (not shown in the drawing) from the interior of the micropore forming device 120. Thus, as shown in FIG. 14, the plurality of micropores (extraction holes) 111 are formed through which body fluid can be extracted from the wrist 110 of the subject since the micropores (extraction holes) 111 are formed through the epidermis to the corium in the wrist 110 of the subject. In this way the discomfort felt by the subject is mitigated when extracting glucose from the wrist 110 of the subject using the blood glucose level measuring device 100. Subsequently, the micropore forming device 120 is detached from the holding member body 21.

Figure 15:
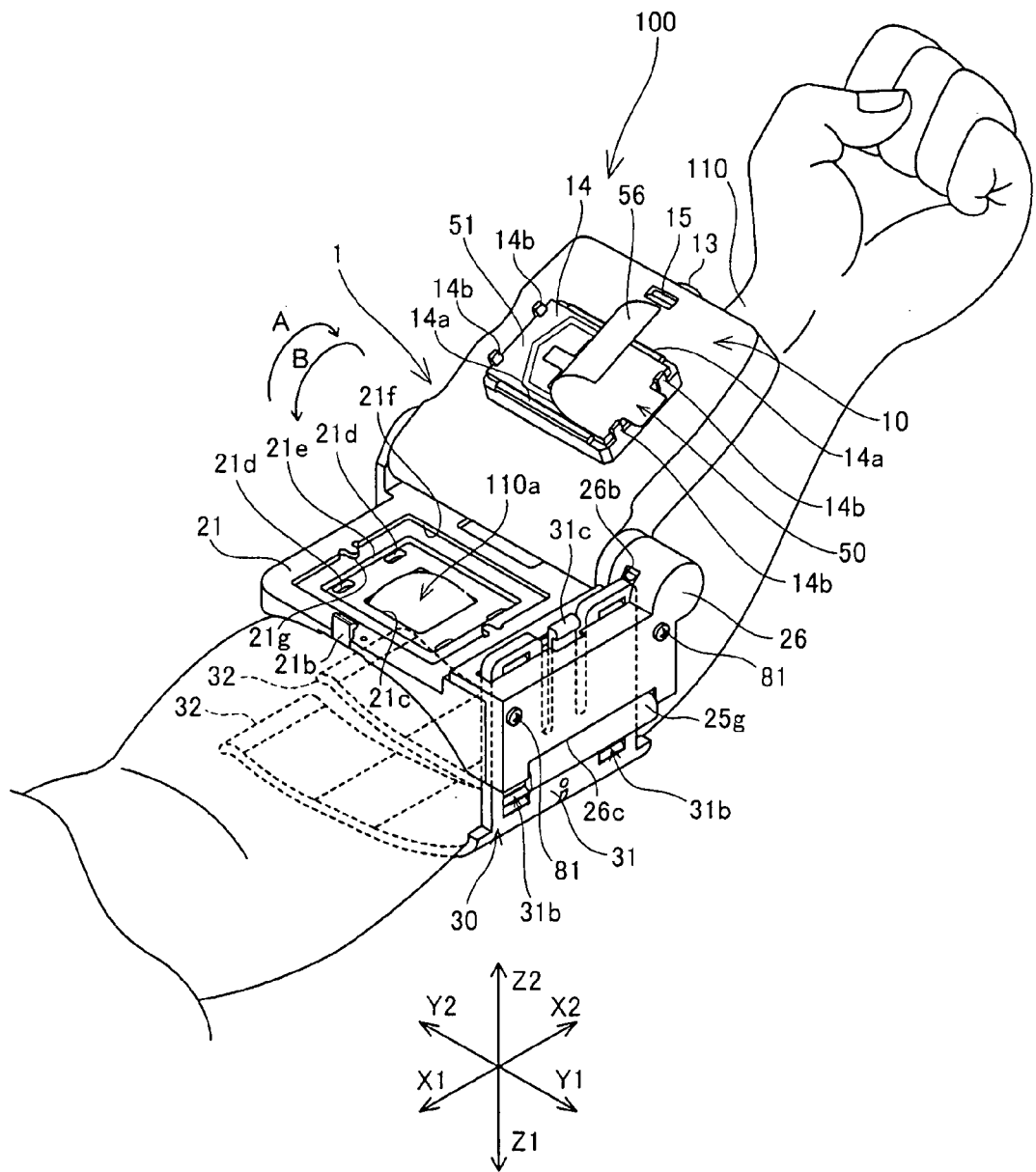

As shown in FIG. 15, in the present embodiment the extraction cartridge 50 is attached on the extraction cartridge attachment part 14 when the device body 10 engages the four connector parts 14b of the extraction cartridge attachment part 14. When the extraction cartridge 50 is attached on the extraction cartridge attachment part 14, a fluid supplying member 56 is attached on the extraction cartridge 50. Then, fluid is supplied from the fluid supplying member 56 to the mesh sheet 52 (refer to FIG. 10) by pressing the fluid supplying member 56 of the extraction cartridge 50 attached on the extraction cartridge attachment part 14. Thereafter, the fluid supplying member 56 is removed from the extraction cartridge 50.

Next, the device body 10 is rotated in the B direction to close the device body 10. Since the connector hole 15 of the device body 10 engages the connectors 21b of the holding member body 21 at this time (refer to FIG. 15), the device body 10 is prevented from rotating in the A direction relative to the holding member body 21. At this time the extraction cartridge 50 makes contact with the wrist 110 of the subject which is exposed through the open part 21c of the holding member body 21, as shown in FIG. 10. Thereafter, as shown in FIG. 12, the operation button 12 of the device body 10 is operated and the glucose extracted from the wrist 110 of the subject is analyzed and the blood glucose level is calculated. After the blood glucose level measurement has been completed by the blood glucose level measuring device 100, the regulation of the ratchet mechanism is released and the mounting member 30 moves in the opposite direction of the arrow Z2 direction by moving the grip part 25g of the engage member 25 of the holding member 20 in the arrow Y1 direction. Thus, the blood glucose level measuring device 100 is detached from the wrist 110 of the subject.

As described above, in the present embodiment, the measuring area 110a is defined when the holding member 20 which can retain the device body 10 and has the open part 21c for defining the measurement area 110a of the wrist 110 of the subject is mounted on the wrist 110 of the subject via the mounting member 30, and thereafter the micropores 111 are formed in the measuring area 110a of the wrist 110 of the subject defined by the open part 21c. Thus, since the microneedles (not shown in the drawing) for forming the micropores 111 are not inserted in the skin when mounting the device body 10 on the holding member 20, the skin is not damaged by the microneedles (not shown in the drawing). Therefore, there is no difficulty in stably extracting and analyzing glucose which might result from damaging the skin when mounting the device body 10 on the holding member 20. As a result, stable glucose extraction and analysis can be performed. Moreover, in the present embodiment after the micropores 111 have been formed the extraction cartridge 50 makes contact with the micropores 111 in the wrist 110 of the subject through the open part 21c, and the glucose extracted by the extraction cartridge 50 is detected by the detecting part 40 (refer to FIG. 10). In this way stable glucose extraction is easily performed from the micropores 111 in the wrist 110 of the subject via the extraction cartridge 50, and stable analysis of the extracted glucose is also performed.

In the present embodiment the extraction cartridge 50 can be replaced because the extraction cartridge 50 is configured so as to be detachably attached on the mounting body 10, and, therefore, glucose extraction and analysis can be performed repeatedly.

In the present embodiment the device body 10 is rotatably mounted on the holding member 20 so as to separate the extraction cartridge 50 from the open part 21c when the extraction cartridge 50 is in contact with the wrist 110 of the subject through the open part 21c. In this way, with the holding member 20 mounted on the wrist 110 of the subject, glucose can be extracted from the micropores 111 on the wrist 110 of the subject via the extraction cartridge 50, and the extraction cartridge 50 of the device body 10 can be replaced, and micropores 111 can be formed in the measuring area 110a on the wrist 110 of the subject via the open part 21c.

In the present embodiment the mounting member 30 is configured to include the tightening parts 32 for tightening the wrist 10 of the subject held between the tightening parts 32 and the holding member 20, and a connector part 31 for connecting the tightening parts 32 and the holding part 20 so as allow a changeable distance between the holding member 20 and the tightening parts 32. Thus, since the connector part 31 regulates the distance between the tightening parts 32 and holding part 20 to a distance corresponding to the size of the wrist 110 of the subject, and the wrist 110 of the subject is easily grasped by the tightening parts 32 and holding part 20 even for different sizes of wrist 110 of the subjects.

In the present embodiment the connector part 31 of the mounting member 30 is configured so as to connect the tightening parts 32 of the mounting member 30 so as to be linearly movable relative to the holding member 20. In this way the holding member 20 can be prevented from moving in the circumferential direction of the wrist 110 of the subject since the wrist 110 of the subject is tightened in a vertical direction by the holding member 20 and tightening parts 32, unlike when straps are used on a mounting member. Moreover, since the wrist 110 of the subject is tightened in a vertical direction by the holding member 20 and tightening parts 32, force is only operative on the skin in a vertical direction and no force is operative in the circumferential direction. Therefore, the formation of micropores 111 and extraction of glucose in the measuring area 110a can be performed easily since the measuring area 110a of the subject wrist 110 is readily expanded through the open part 21c of the holding member 20.

In the present embodiment one end of the holding member 20 and tightening parts 32 (end in the arrow Y1 direction) are connected by the connector part 31, and the other end of the holding member 20 and tightening parts 32 (end in the arrow Y2 direction) are mutually separated. Thus, the wrist 110 of the subject is readily positioned in the area between the holding member 20 and tightening parts 32 since the subject wrist 110 is inserted from a lateral direction through the area in which the other end of the holding member 20 and tightening parts 32 are mutually separated. Thus, the workability of the mounting operation is improved since the wrist 110 of the subject is readily tightened between the holding member 20 and tightening parts 32. Moreover, the workability when detaching the device is also improved since the subject wrist 110 can be directly pulled out through the area in which the holding member 20 and tightening parts 32 are mutually separated when some anomaly has occurred during glucose extraction and analysis by the blood glucose level measuring device 100. As a result, the workability of both the mounting and detaching operations are improved.

In the present embodiment the two tightening parts 32 of the mounting member 30 are configured so as to be elastically deformable to readily make contact with the wrist 110 of the subject when the wrist 110 is held between the tightening parts 32 and the holding member 20. Therefore, since the tightening parts 32 closely contact with the subject wrist 10, the holding member 20 is prevented from moving relative to the subject wrist 110.

In the present embodiment the connector part 31 of the mounting member 30 includes connecting areas 31b configured as a ratchet mechanism for unidirectionally regulating the direction of movement of the tightening parts 32 relative to the holding member 20, and the holding member 20 is configured to include a engage member 25 as a ratchet mechanism as well as connecting area 31b as a ratchet mechanism of the connector part 31. Thus, the subject wrist 10 can be fixedly held between the holding member 20 and the tightening parts 32 since the tightening parts 32 are only allowed to move unidirectionally (arrow Z2 direction) relative to the holding member 20 by the ratchet mechanism configured by the engage member 25 of the holding member 20 and the connecting areas 31b of the connector part 31.

In the present embodiment the engage member 25 of the holding member 20 includes the release function of releasing the regulation of the ratchet mechanism. Therefore, the release function of the engage member 25 can be set to a condition in which a condition in which the tightening parts 32 are separated from the subject wrist 110, from a condition in which the subject wrist 110 is fixedly held between the tightening parts 32 and the holding member 20.

The present embodiment is provided with a constant voltage regulated power supply 17 for supplying a voltage, the extraction cartridge 50 includes an electrode 53 connected to the negative pole of the constant voltage power supply 17, and the mounting member 30 and holding member body 21 of the holding member 20 are used as electrodes connected to the positive pole of the constant voltage power supply 17. The amount of current flowing per unit surface area of the subject wrist 10 can be reduced since the surface area of the electrodes is increased by using the mounting member 30 and holding member body 21 as electrodes connected to the constant voltage regulated power supply 17. Thus, the discomfort experienced by the subject caused by the flowing current can be minimized.

The embodiment of the present disclosure is to be considered in all aspects an example and in no manner limiting. The scope of the present invention is described by the scope of the claims and not by the description of the previously mentioned embodiment, and should be construed as including all meanings and equivalences within the scope of the claims.

For example, although the present embodiment has been described in terms of a blood glucose level measuring device as an example of a biological component measuring device, the present invention is not limited to this device inasmuch as the invention is also applicable to other biological component measuring devices.

Although an example of a holding member 20 provided with an open part 21c holding the analyzing unit 1 is used in the present embodiment, the present invention is not limited to this configuration insofar as the a holding member provided with an open part and an analysis unit may be provided separately such that the analysis unit is held by the holding member when glucose is extracted and analyzed.

Figure 16:
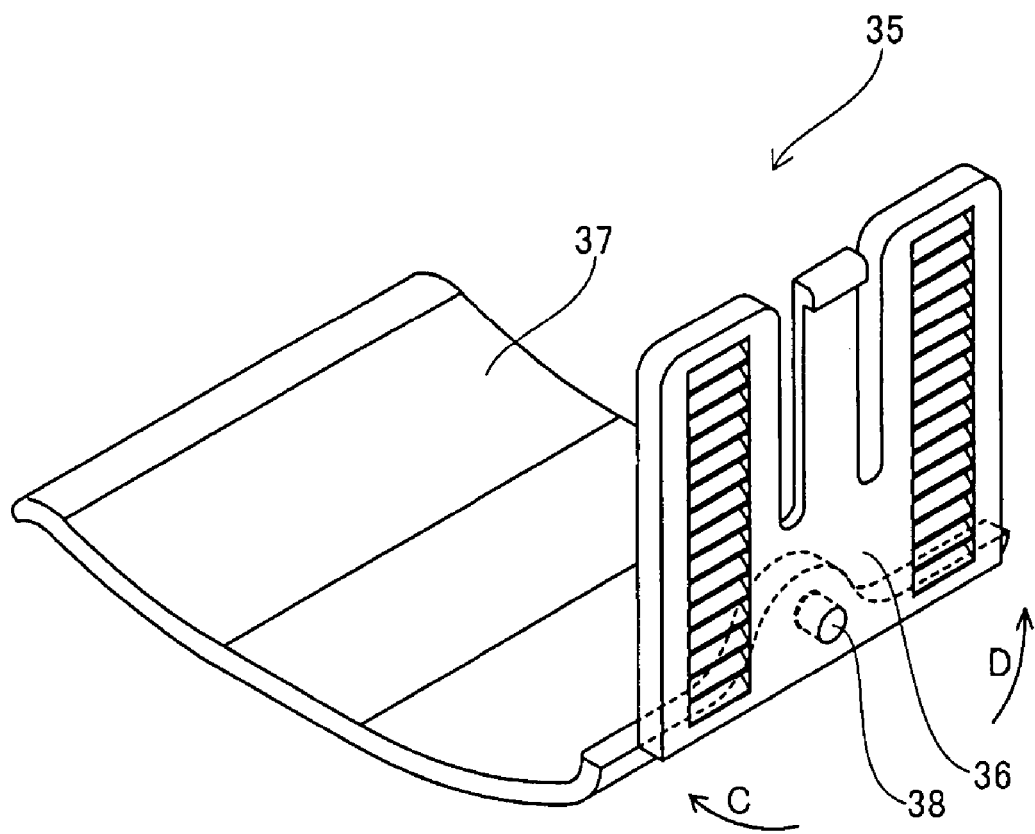
FIG. 16 is a perspective view of a variation of the mounting member of the embodiment of the blood glucose level measuring device of the present invention.

Although the mounting member 30 includes two elastically deformable tightening parts 32 in the example of the embodiment, the present invention is not limited to this configuration insofar as the mounting member includes a tightening part to easily make contact the wrist of a subject. Specifically, a single tightening part 37 may be provided on a connector member 36 so as to be mounted and rotated in the C direction and D direction relative to the connector member 36 via a rotating shaft 38 as in the mounting member 35 of a modification of the embodiment shown in FIG. 16. Moreover, the mounting member may also be provided with three or more elastically deformable tightening parts.

Although an example using both the holding member body 21 and mounting member 30 as electrodes was described in the embodiment, the present invention is not limited to this configuration inasmuch as either the holding member body or the mounting member alone may be used as an electrode.

Although an example of gold plating on the inner surface (cross hatched area of FIG. 9) of the mounting member 30 and the periphery of the bottom surface and L-shaped projection 21l of the holding member body 21 (cross hatched areas of FIGS. 5 and 6) is described in the embodiment, the present invention is not limited to this configuration inasmuch as an electrically conductive sheet member may also be provided on the inner surface (cross hatched (diagonal line) area of FIG. 9) of the mounting member 30 and the periphery of the bottom surface and L-shaped projection 21l of the holding member body 21 (cross hatched (diagonal line) areas of FIGS. 5 and 6).

Although an example of attaching the cover member 26 on the holding member body 21 using the screws 81 is described in the embodiment, the present invention is not limited to this configuration inasmuch as the cover member may also be press-fit on the holding member body.

What is claimed is:

1. A measuring device, comprising:
a device body which comprises an extraction part for extracting body fluid from a living body and a measuring part for measuring a biological component contained in the extracted body fluid;
a holding member which holds the device body and has an opening part for defining a measurement area on the living body; and
a mounting member for mounting the holding member on the living body;
wherein the measurement area on the living body is defined by the opening part when the holding member is mounted on the living body by the mounting member, and
wherein the mounting member comprises a tightening part which is configured to tighten the living body between the tightening part and the holding part, and a connecting part which connects the tightening part and the holding part so that a distance between the tightening part and the holding part is changeable.

2. The measuring device of claim 1,
wherein the opening part of the holding member is configured to receive a micropore forming device for forming a micropore on the living body to form a micropore in the measurement area via the opening part, and
wherein the extraction part is configured to extract the body fluid from the micropore formed by the micropore forming device.

3. The measuring device of claim 1, wherein
the extraction part is detachably attached to the device body.

4. The measuring device of claim 1,
wherein the device body is held by the holding member so that the measuring device has a first state and a second state, and
wherein, in the first state, the extraction part contacts the living body via the opening part, and in the second state, the extraction part is separated from the living body.

5. The measuring device of claim 4, wherein
the device body is held by the holding member so that the device body is movable relative to the holding member, and the measuring device changes between the first state and the second state by movements of the device body.

6. The measuring device of claim 1, wherein
the connecting part connects the tightening part to the holding part so that the tightening part is linearly movable relative to the holding part.

7. The measuring device of claim 1, wherein
one end of the holding part and one end of the tightening part are connected by the connecting part, and the other end of the holding part and the other end of the tightening part are separated from each other.

8. The measuring device of claim 1, wherein
the measurement area is defined by the opening part when the living body is held between the tightening part and the holding member.

9. The measuring device of claim 1, wherein
the tightening part is flexible so as to become in close contact with the living body while the living body is held between the tightening part and the holding member.

10. The measuring device of claim 1, wherein
a surface of the tightening part, which is facing the holding member, is formed concavely.

11. The measuring device of claim 1, wherein
a surface of the holding member, which is facing the tightening part, is formed concavely.

12. The measuring device of claim 1,
wherein the connecting part comprises a first part, and the holding member comprises a second part, and
wherein the first part and the second part form a ratchet mechanism which regulates a moving direction of the tightening part relative to the holding member.

13. The measuring device of claim 12, wherein
the ratchet mechanism allows the tightening part to move toward the holding member and restricts the tightening part from moving in a separating direction from the holding member.

14. The measuring device of claim 13, wherein
the second part of the holding member comprises a release mechanism which releases the tightening part from restriction by the ratchet mechanism on moving in the separating direction.

15. The measuring device of claim 1, further comprising
a power source for supplying a voltage,
wherein the extraction part comprises a first electrode connected to one pole of the power source, and at least one of the holding member and the mounting member is used as a second electrode connected to the other pole of the power source so that the power source supplies a voltage to the living body through the first electrode and the second electrode.

16. The measuring device of claim 1, wherein
a contact surface of at least one of the holding member and the mounting member, which contacts the living body, is formed of an electrically conductive material.

17. A measuring device, comprising:
a device body which comprises an extraction part for extracting body fluid from a living body and a measuring part for measuring a biological component contained in the extracted body fluid;
an area defining member which has an opening part for defining a measurement area on the living body and to which the device body is detachably attached; and
a mounting member for mounting the area defining member on the living body;
wherein the measurement area on the living body is defined by the opening part when the area defining member is mounted on the living body by the mounting member, and
the mounting member comprises a tightening part which is configured to tighten the living body between the tightening part and the holding part, and a connecting part which connects the tightening part and the area defining member so that a distance between the tightening part and the area defining member is changeable.

* * * * *